United States Patent
Yang et al.

(10) Patent No.: US 11,875,433 B2
(45) Date of Patent: *Jan. 16, 2024

(54) SYSTEM AND METHOD FOR SCATTER CORRECTION

(71) Applicant: SHANGHAI UNITED IMAGING HEALTHCARE CO., LTD., Shanghai (CN)

(72) Inventors: Hongcheng Yang, Shanghai (CN); Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 140 days.

This patent is subject to a terminal disclaimer.

(21) Appl. No.: 17/444,744

(22) Filed: Aug. 9, 2021

(65) Prior Publication Data

US 2021/0366167 A1 Nov. 25, 2021

Related U.S. Application Data

(63) Continuation of application No. 16/232,016, filed on Dec. 25, 2018, now Pat. No. 11,087,507, which is a (Continued)

(51) Int. Cl.
*G06T 7/11* (2017.01)
*G06T 11/00* (2006.01)
(Continued)

(52) U.S. Cl.
CPC ............ *G06T 11/005* (2013.01); *A61B 6/032* (2013.01); *A61N 5/1039* (2013.01); *G06T 7/11* (2017.01);
(Continued)

(58) Field of Classification Search
CPC ...................................................... G06T 11/005
See application file for complete search history.

(56) References Cited

U.S. PATENT DOCUMENTS

| 8,144,829 B2 | 3/2012 | Zhu et al. |
| 2003/0073893 A1 | 4/2003 | Hsieh |

(Continued)

FOREIGN PATENT DOCUMENTS

| CN | 105574828 A | 5/2016 |
| CN | 108542414 A | 9/2018 |
| CN | 108957515 A | 12/2018 |

OTHER PUBLICATIONS

International Search Report in PCT/CN2018/111764 dated Jun. 27, 2019, 7 pages.

(Continued)

*Primary Examiner* — Oneal R Mistry
(74) *Attorney, Agent, or Firm* — METIS IP LLC

(57) ABSTRACT

The present disclosure provides a method for processing projection data. The method may include obtaining a first image generated by performing a first scan to a subject by a first imaging device; determining first projection data based on the first image, the first projection data corresponding to a first area of the subject; obtaining second projection data by performing a second scan of the subject using a second imaging device, the second projection data corresponding to a second area of the subject, the first area at least partially overlapping with the second area in an overlapping area; determining registered first projection data by registering the first projection data to the second projection data with respect to the overlapping area; determining scatter component based on the registered first projection data and the second projection data, the scatter component including low-frequency scattered radiation signals.

19 Claims, 10 Drawing Sheets

Related U.S. Application Data continuation of application No. PCT/CN2018/111764, filed on Oct. 25, 2018.

(51) Int. Cl.
    *A61N 5/10*     (2006.01)
    *A61B 6/03*     (2006.01)

(52) U.S. Cl.
    CPC .... *G06T 11/008* (2013.01); *A61N 2005/1061* (2013.01); *G06T 2207/10081* (2013.01); *G06T 2211/424* (2013.01)

(56) References Cited

U.S. PATENT DOCUMENTS

| | | | | |
|---|---|---|---|---|
| 2012/0069953 | A1* | 3/2012 | Chandra | G21K 1/10 378/19 |
| 2012/0213424 | A1 | 8/2012 | Flohr et al. | |
| 2012/0263360 | A1* | 10/2012 | Zhu | G06T 11/005 382/131 |
| 2013/0004042 | A1* | 1/2013 | Yang | A61B 6/032 382/131 |
| 2016/0054453 | A1* | 2/2016 | Moriyasu | A61B 6/4035 378/19 |
| 2017/0116762 | A1* | 4/2017 | Lin | A61B 6/025 |
| 2017/0340304 | A1* | 11/2017 | Qiulin | A61B 6/5205 |
| 2018/0284035 | A1* | 10/2018 | Steadman Booker | A61B 6/032 |
| 2019/0043187 | A1* | 2/2019 | Kuusela | A61B 6/032 |
| 2019/0080491 | A1* | 3/2019 | Saito | G06T 11/006 |

OTHER PUBLICATIONS

Written Opinion in PCT/CN2018/111764 dated Jun. 27, 2019, 6 pages.

* cited by examiner

SYSTEM AND METHOD FOR SCATTER CORRECTION

CROSS-REFERENCE TO RELATED APPLICATIONS

This application is a continuation of U.S. patent application Ser. No. 16/232,016, filed on Dec. 25, 2018, which is a continuation of International Application No. PCT/CN2018/111764, filed on Oct. 25, 2018, the entire contents of which are hereby incorporated by reference.

TECHNICAL FIELD

The present disclosure generally relates to systems and methods for scatter correction in image processing, and more particularly, to systems and methods for correcting scatter radiation signals of computed tomography (CT) projection data based on a prior scatter-free image.

BACKGROUND

In addition to its widespread use in medical diagnostic imaging, computed tomography (CT) has been increasingly applied in patient positioning and verification in image-guided radiation therapy (IGRT). CT projection data may be largely contaminated by scatter radiation signals due to large radiation field of view. The increased scatter radiation signals may decrease image contrast, CT number accuracy, and may lead to severe cupping artifact in the reconstructed image, which limits the potential use of dose calculation and tumor delineation for adaptive radiation therapy.

SUMMARY

According to an aspect of the present disclosure, a system configured to process projection data is provided. The system may include at least one non-transitory storage medium including a set of instructions; and at least one processor in communication with the at least one non-transitory storage medium. When executing the set of instructions, the at least one processor may be configured to direct the system to obtain a first image generated by performing a first scan to a subject by a first imaging device; determine first projection data based on the first image, the first projection data corresponding to a first area of the subject; obtain second projection data by performing a second scan of the subject using a second imaging device, the second projection data corresponding to a second area of the subject, the first area at least partially overlapping with the second area in an overlapping area; determine registered first projection data by registering the first projection data to the second projection data with respect to the overlapping area; determine scatter component based on the registered first projection data and the second projection data, the scatter component including low-frequency scattered radiation signals; and, determine corrected second projection data based on the scatter component and the second projection data.

In some embodiments, to determine the first projection data based on the first image, the at least one processor may be further configured to direct the system to: determine the first projection data based on a physical density distribution related to the first image and a material distribution related to the first image.

In some embodiments, the physical density distribution related to the first image may be determined based on CT numbers of the first image.

In some embodiments, to determine the material distribution related to the first image, the at least one processor may be further configured to direct the system to: segment the first image into one or more regions based on the physical density distribution related to the first image or the CT numbers of the first image, each of the one or more regions corresponding to a composition category of the subject; and determine the material distribution related to the first image based on the one or more regions corresponding to a composition category of the subject.

In some embodiments, the second scan may be performed using energy beams of one or more energy spectra generated by the second device, and the first projection data may be further determined based on the energy spectra and detector energy response of the second device, and to determine first projection data based on the first image and the energy spectra and detector energy response of the second device, the at least one processor may be further directed to: divide, based on an energy range metric, the energy spectrum of the energy beams related to the second scan into one or more bins, each bin corresponding to an energy range; for each of the one or more bins, determine simulated projection data based on the first image and an energy range corresponding to the bin; and combine the simulated projection data of the one or more bins to generate the first projection data.

In some embodiments, the simulated projection data of each of the one or more bins may correspond to a plurality of voxels, and to determine the simulated projection data corresponding to a bin, the at least one processor may be further configured to direct the system to: convert the first image into a physical density distribution; segment, based on the physical density distribution or CT numbers of the first image, the first image into one or more categories; and for each of the one or more bins, determine, based on the one or more categories and the energy range corresponding to the bin, a mass attenuation coefficient matrix for the plurality of voxels corresponding to the bin; determine, based on the mass attenuation coefficient matrix and the physical density distribution, a linear attenuation coefficient matrix corresponding to the bin; and determine, based on the linear attenuation coefficient matrix, the simulated projection data of the bin.

In some embodiments, for each of the one or more bins, the at least one processor may be further directed to: determine the simulated projection data based on detector energy response corresponding to the energy range.

In some embodiments, the registration of the first projection data to the second projection data may be a two-dimensional registration.

In some embodiments, the first image may include first isocenter information, and the second scan is performed based on the first isocenter information.

In some embodiments, the first projection data may be determined based on the first isocenter information.

In some embodiments, to determine corrected second projection data based on the scatter component and the second projection data, the at least one processor may be further configured to direct the system to: divide the scatter component into one or more groups; for each of the one or more groups, determine whether a group satisfies a first condition; and generate, based on the scatter component of the group and a result of the determination, trusted scatter component; and determine the corrected second projection data based on the trusted scatter component.

In some embodiments, the first condition may be that the scatter component of the each group is positive and lower than a threshold.

In some embodiments, the first condition may be that a gradient of the scatter component of the each group is lower than a threshold.

In some embodiments, the first condition may be that a ratio of a sum of the registered first projection data in a group and the scatter component in the group to the second projection data in the group may be within a certain range.

In some embodiments, the first imaging device may be a multiple-detector computed tomography device, and the second imaging device may be a cone beam computed tomography device.

According to an aspect of the present disclosure, a system configured to process projection data is provided. The system may include at least one non-transitory storage medium including a set of instructions; and at least one processor in communication with the at least one non-transitory storage medium. When executing the set of instructions, the at least one processor may be configured to direct the system to obtain a first image corresponding to a first area of the subject; obtain second projection data related to an energy spectrum and a detector energy response of a cone-beam computed tomography, the second projection data corresponding to a second area of the subject, the first area at least partially overlapping with the second area in an overlapping area; determine first projection data based on the first image, the energy spectrum and the detector energy response of the cone-beam computed tomography; determine scatter component based on the first projection data and the second projection data.

According to an aspect of the present disclosure, a system configured to process projection data is provided. The system may include at least one non-transitory storage medium including a set of instructions; and at least one processor in communication with the at least one non-transitory storage medium. When executing the set of instructions, the at least one processor may be configured to direct the system to obtain initial projection data by a cone-beam computed tomography; reconstruct one or more uncorrected images based on the initial projection data; determine stimulated projection data based on the one or more uncorrected images; determine scatter components based on stimulated projection data and the initial projection data by subtracting the simulated projection data from the initial projection data; correct the initial projection data by subtracting the scatter components from the initial projection data to generate corrected initial projection data; perform one or more iterations, each current iteration of the one or more iterations including: assigning the corrected initial projection data of the last iteration as the initial projection data of the current iteration; correcting the initial projection data in each current iteration to generate corrected initial projection data according to the process for correcting initial projection data.

According to an aspect of the present disclosure, a method for processing projection data is provided. The method may be implemented on at least one machine each of which has at least one processor and storage. The method may include obtaining a first image generated by performing a first scan to a subject by a first imaging device; determining first projection data based on the first image, the first projection data corresponding to a first area of the subject; obtaining second projection data by performing a second scan of the subject using a second imaging device, the second projection data corresponding to a second area of the subject, the first area at least partially overlapping with the second area in an overlapping area; determining registered first projection data by registering the first projection data to the second projection data with respect to the overlapping area; determining scatter component based on the registered first projection data and the second projection data, the scatter component including low-frequency scattered radiation signals; and, determining corrected second projection data based on the scatter component and the second projection data.

According to an aspect of the present disclosure, a method for processing image data is provided. The method may be implemented on at least one machine each of which has at least one processor and storage. The method may include obtaining a first image corresponding to a first area of the subject; obtaining second projection data related to an energy spectrum and a detector energy response of a cone-beam computed tomography, the second projection data corresponding to a second area of the subject, the first area at least partially overlapping with the second area in an overlapping area; determining first projection data based on the first image, the energy spectrum and the detector energy response of the cone-beam computed tomography; determining scatter component based on the first projection data and the second projection data.

According to an aspect of the present disclosure, a method for processing image data is provided. The method may be implemented on at least one machine each of which has at least one processor and storage. The method may include obtaining initial projection data by a cone-beam computed tomography; reconstructing one or more uncorrected images based on the initial projection data; determining stimulated projection data based on the one or more uncorrected images; determining scatter components based on stimulated projection data and the initial projection data by subtracting the simulated projection data from the initial projection data; correcting the initial projection data by subtracting the scatter components from the initial projection data to generate corrected initial projection data; performing one or more iterations, each current iteration of the one or more iterations including: assigning the corrected initial projection data of the last iteration as the initial projection data of the current iteration; correcting the initial projection data in each current iteration to generate corrected initial projection data according to the process for correcting initial projection data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
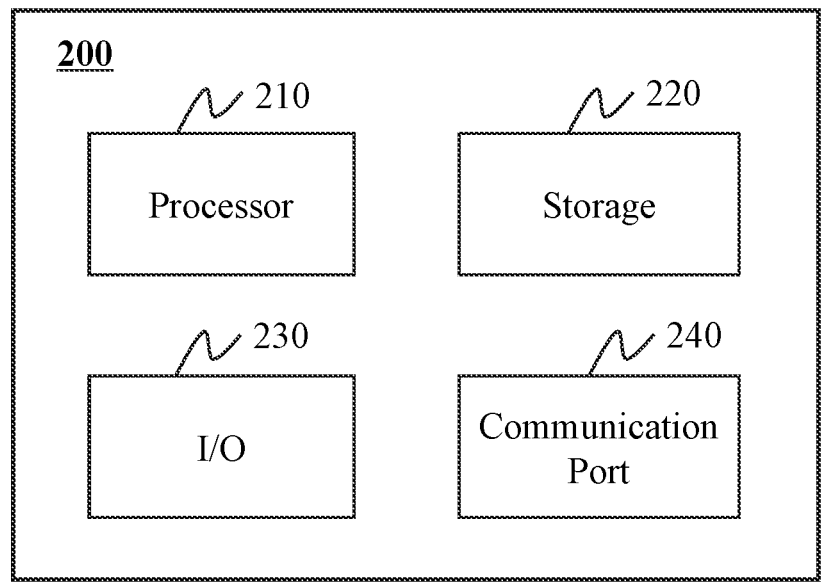
FIG. 2 is a schematic diagram illustrating an exemplary computing device on which the can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when as used herein, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and methods for imaging, such as for disease diagnosis, physical check-up, or disease treatment. For example, the imaging systems and methods provided in the present disclosure may be used in an internal inspection (e.g., a non-invasive internal inspection) including, for the anatomical structure of one or more tissues or one or more organs, the metabolism of one or more tissues or one or more organs, the function of one or more tissues or one or more organs. The imaging system may find its applications in different fields other than the medical fields. For example, the imaging system may be used in an internal inspection (e.g., a non-invasive internal inspection) of one or more components. For example, the imaging systems and methods provided in the present disclosure may be used in flaw detection of a component of a machine, bag or luggage security scanning, failure analysis, metrology, assembly analysis, void detection, wall thickness assessment, or the like, or any combination thereof.

Some embodiments of the present disclosure provide systems and methods for correcting CT projection data. In some embodiments, a prior scatter-free image of a subject may be obtained first. The prior scatter-free image may be used to generate projection data only containing primary radiation signals, which may be registered with the CT projection data. To generate the projection data containing only primary radiation signals based on the prior scatter-free image, material categories of the subject, detector energy response and/or an energy spectrum of the X-ray beams used to generate the primary radiation signals may be taken into consideration, which may improve the accuracy of the forward projection. The information of said detector energy response and energy spectrum is from a cone-beam computed tomography system. The corrected CT projection data may be determined based on the projection data containing only primary radiation signals after registration and the CT projection data. The registration may be two-dimensional, which may reduce the registration time compared to a 3D image registration. In some embodiments, a corrected image may then be reconstructed based on the corrected projection data. The corrected image or the corrected projection data may then be used for in-vivo an electronic portal image device (EPID) based dose verification.

The following description is provided to facilitate better understanding of CT projection data correction methods and/or systems. The term "image" used in this disclosure may refer to a 2D image, a 3D image, a 4D image, and/or any related image data (e.g., projection data and/or corresponding image data). The image data may correspond to a distribution of the degree of absorption of X-ray beams by different anatomical structures of the subject (e.g., a patient). The projection data corresponding to the image data may refer to a sum or line integral of linear attenuation coefficient (s) along a plurality of X-ray beam directions.

The following descriptions in connection with a CBCT imaging system are provided for illustration purposes. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
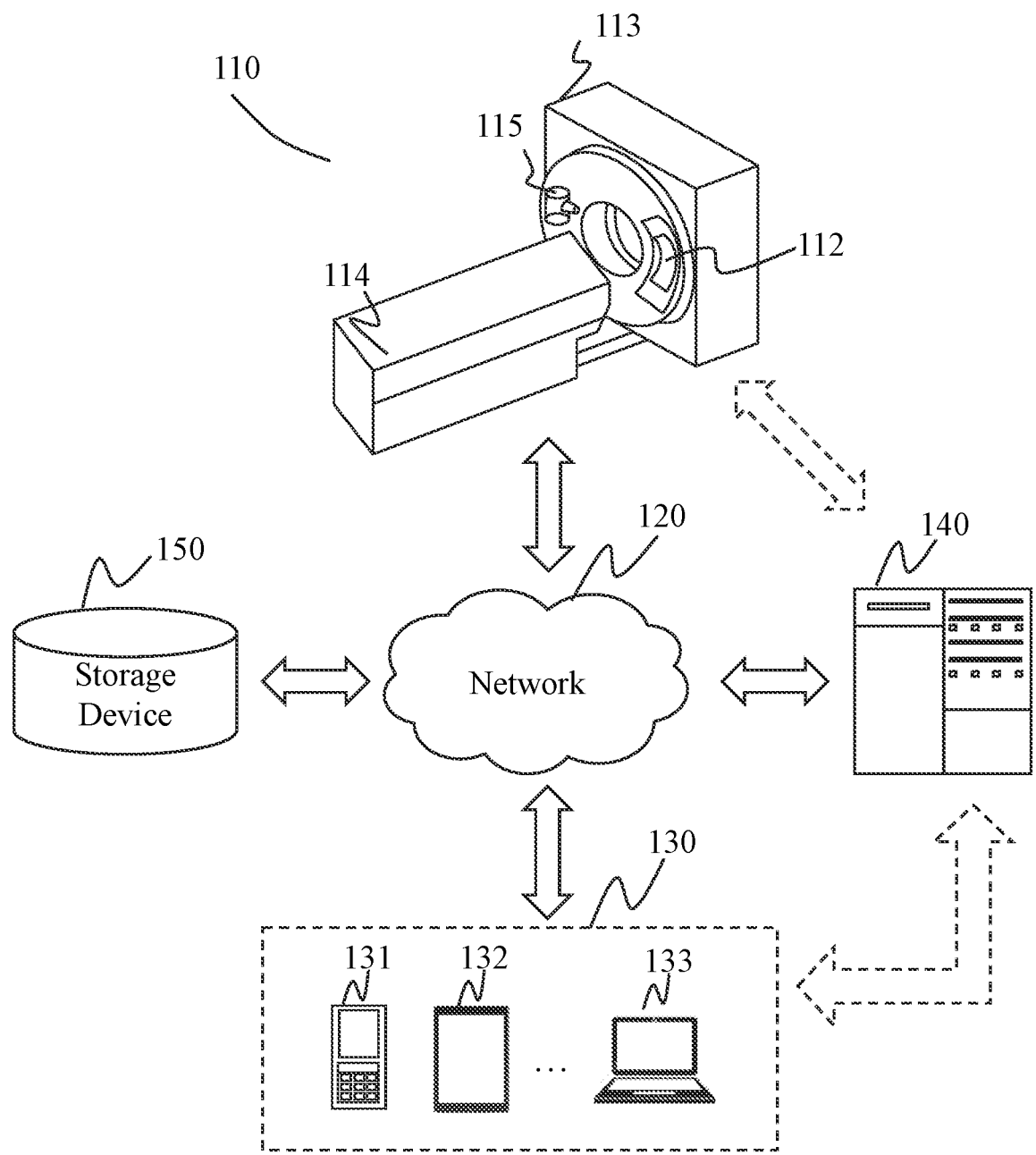
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. The imaging system 100 may include one or more imaging devices 110, a network 120, one or more terminals 130, a processing device 140, and a storage device 150.

The one or more imaging devices 110 may include a first image device and/or a second imaging device. An imaging device 110 may be a computed tomography (CT) imaging device, a magnetic resonance image (MM) device, or a positron-emission tomography (PET) imaging device, etc. Scatter radiation of the first imaging device may be smaller than the second imaging device, and therefore the first imaging device can acquire images of better quality. Merely by way of example, the first imaging device may be a multi-detector computed tomography (MDCT) imaging device, and the second imaging device may be a cone beam computed tomography (CBCT) imaging device. For example, the one or more imaging devices are CT imaging device (e.g., MDCT imaging device or CBCT imaging device), the imaging device 110 may include a gantry 113, a detector 112, a table 114, and a scanning source 115. The gantry 113 may support the detector 112 and the scanning source 115. A subject may be placed on the table 114 for scanning. The scanning source 115 may emit X-rays to the subject. The detector 112 may detect attenuated X-rays. The attenuated X-rays may further be processed and converted to image data for image reconstruction. Merely by way of example with reference to an imaging system 100, the X-rays may be generated by the scanning source 115 according to the bremsstrahlung principle, and generally an energy spectrum of the X-rays may be continuous. The detector 112 may include a semiconductor detector, a gas detector, or a scintillation detector, etc. In some embodiments, the detector 112 may include a plurality of detector units, and the plurality of detector units may be arranged in any suitable manner. For example, the plurality of detector units may be arranged on a plane, and the detector 112 may be a flat panel detector. As another example, the plurality of detector units may be arranged on an arc surface, and the detector 112 may be an arc-shaped detector.

In some embodiments, some x-rays may be scattered by the subject itself or one or more components of the imaging device 110, and thus scattered radiations may be received by the detector 112, which may cause imaging quality degradation in an image converted by signals from the imaging device 110. For example, the scattered radiation may cause scatter artifacts (e.g., shading/cupping artifacts).

In some embodiments, a treatment device (not shown in the figure) may be added to the imaging system 100. The treatment device may include a treatment radiation source, a gantry, a collimator, or the like, or a combination thereof. The treatment radiation source may be a linear accelerator (LINAC). The collimator may control the shape of the radioactive rays generated by the treatment radiation source. In some embodiments, the imaging device 110 and the treatment device may share a same gantry. For example, the treatment radiation source may be mounted on the gantry 113. A subject may be placed on the table 114 for treatment and/or scan. Merely by way of example with reference to a radiation therapy device, the imaging system 100 may be an RT-CT system. The imaging device 110 described herein may be applied in subject positioning and/or verification in image-guided radiation therapy (IGRT). The image for guiding a radiation therapy may be generated based on the image data processed/converted from the attenuated X-rays detected by the detector 112 of the imaging device 110.

The network 120 may include any suitable network that can facilitate the exchange of information and/or data for the imaging system 100. In some embodiments, one or more components of the imaging system 100 (e.g., the imaging device 110, the terminal(s) 130, the processing device 140, the storage device 150, etc.) may exchange information and/or data with one or more other components of the imaging system 100, or an external device (e.g., an external storage device) via the network 120. For example, the processing device 140 may obtain projection data from the imaging device 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 702.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

Figure 3:
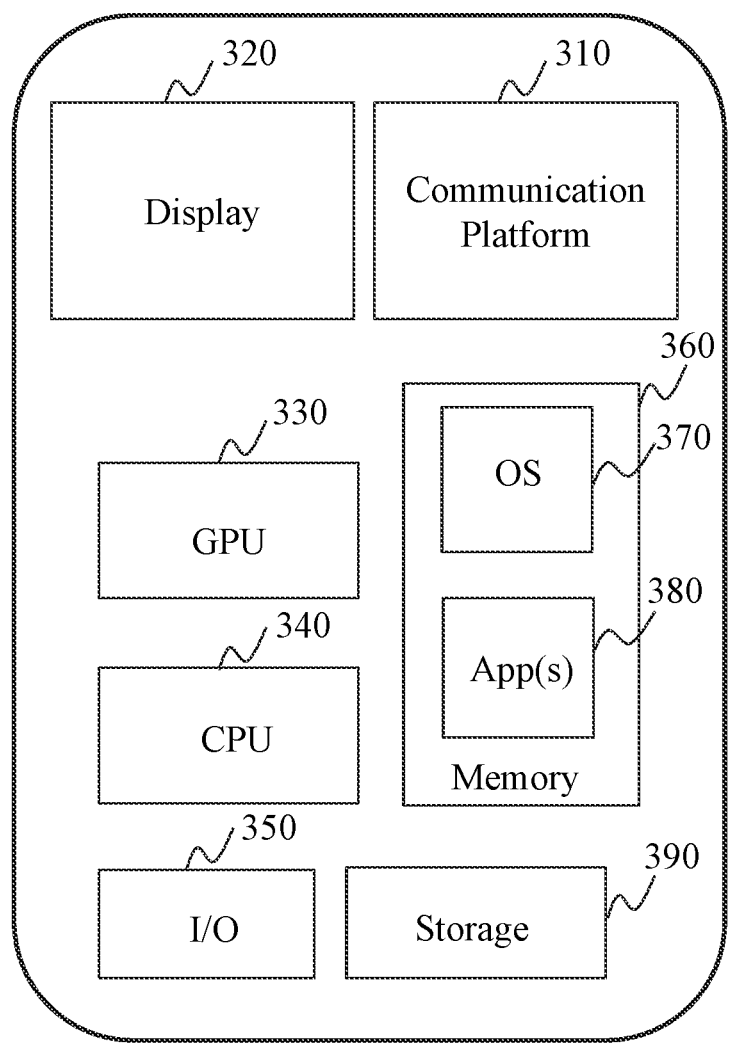
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof In some embodiments, the wearable device may include a bracelet, footwear, eyeglasses, a helmet, a watch, clothing, a backpack, a smart accessory, or the like, or any combination thereof In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™ an Oculus Rift™, a Hololens™, a Gear VR™, etc. In some embodiments, the terminal(s) 130 may be part of the processing device 140.

The processing device 140 may process data, images, and/or information obtained from the imaging device 110, the terminal(s) 130, the storage device 150, an external device, etc. In some embodiments, the processing device 140 may be a single server or a server group. The server group may be centralized or distributed. In some embodiments, the processing device 140 may be local or remote. For example, the processing device 140 may access, via the network 120, data, images, and/or information stored in the imaging device 110, the terminal(s) 130, the storage device 150, an external device, etc. As another example, the processing device 140 may be directly connected to the imaging device 110, the terminal(s) 130, and/or the storage device 150 to access stored data, images, and/or information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal(s) 130). In some embodiments, the storage device 150 may be part of the processing device 140.

FIG. 2 is a schematic diagram illustrating an exemplary computing device 200 on which at least a portion of the imaging system 100 can be implemented, according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process projection data obtained from the imaging device 110, the terminal(s) 130, the storage device 150, and/or any other component of the imaging system 100. As another example, the processor 210 may process image(s) obtained from the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus, operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the imaging system 100, an external device, etc. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for scatter correction.

The I/O 230 may input and/or output signals, data, information, etc. In some embodiments, the I/O 230 may enable user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
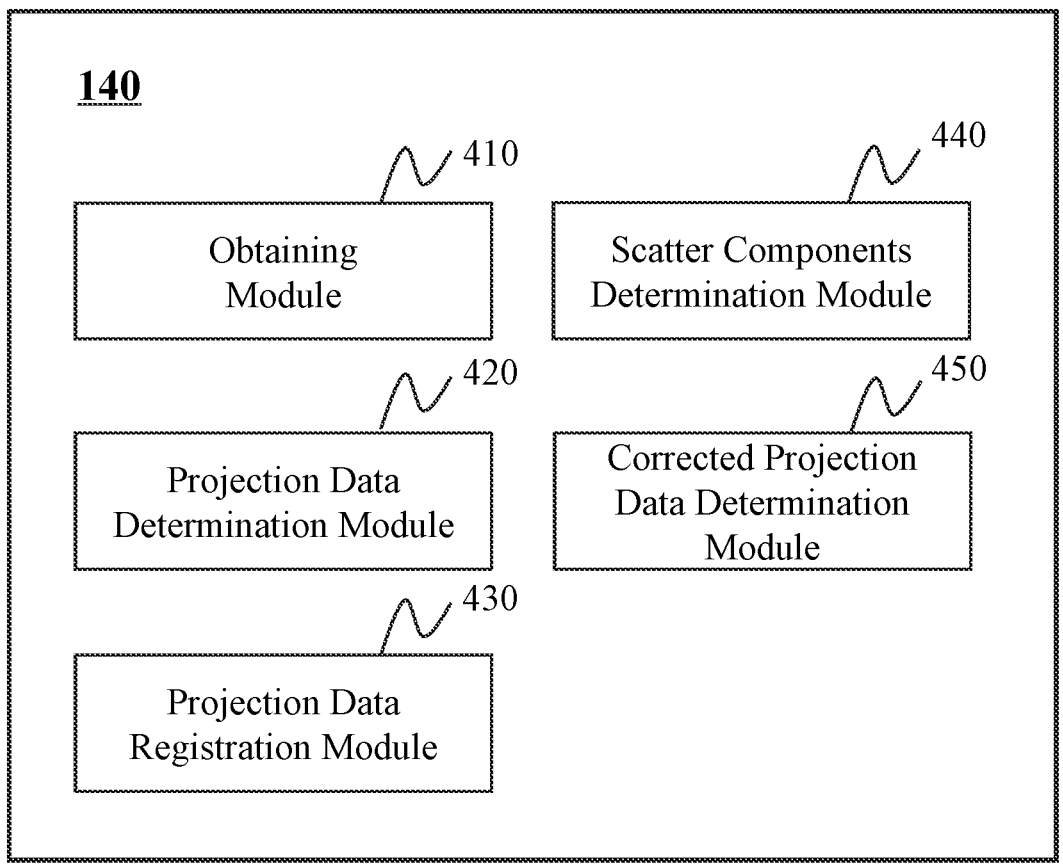
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an obtaining module 410, a projection data determination module 420, a projection data registration module 430, a sactter component determination module 440, and a corrected projection data determination module 450. The processing device 140 may be implemented on various components (e.g., the computing device 200 as illustrated in FIG. 2, the mobile device 300 as illustrated in FIG. 3).

The obtaining module 410 may be configured to obtain a plurality of first images by performing a first scan of a subject using energy beams generated by a first imaging device. A first image in the present disclosure may refer to a reference image with relatively fewer scatter artifacts than a to-be-corrected image, and the scatter artifacts of the to-be-corrected image may be corrected based on the first image as prior information. The first image may include a CT image, a fluoroscopy image, an ultrasound image, a PET image, or an MRI image, etc. Merely by way of example with reference to a radiation treatment, the first image may be a planning image according to which a treatment plan is made. The treatment plan may describe how a radiation treatment is performed on a subject (e.g., patient). In some embodiments, the first imaging device may be a multi-detector computed tomography (MDCT) device, and the first scan is an MDCT scan. With fewer scatter radiation signals than a CBCT device, the MDCT scan may be used for radiation treatment planning. For example, in the image-guided radiation therapy (IGRT), MDCT, because of the high image quality it provides, may be used to generate planning image for treatment plan determination, and CBCT, because of the relative faithful accuracy and a shorter imaging time it provides, may be used to provide position information during the performance of the IGRT. According to some embodiments of the present disclosure, the MDCT image (e.g., the first image) may serve as prior information to correct the CBCT image.

In some embodiments, the first image may relate to a treatment isocenter assigned by doctors or physicists. After coarse initial patient positioning, the treatment isocenter of the first image may be close to a machine isocenter of the second imaging device at which the energy beams emitted from different gantry angles intersect.

In some embodiments, the first image may be generated by the MDCT imaging device in advance, and may be stored in the storage device 150. In some embodiments, the obtaining module 410 may acquire the first image from the storage device 150 via the network 120. In some embodiments, the first image may generally refer to any reconstructed image of the subject without or with fewer scattered radiation signals.

In some embodiments, the obtaining module 410 may be configured to obtain second projection data by performing a second scan of the subject using a second imaging device. A plurality of second images may be reconstructed based on the second projection data. A second image in the present disclosure may refer to the to-be-corrected image with relatively more scatter components than the first image since the projection data of the to-be-corrected image may include the scatter component as mentioned before, and the scatter components of the second image may be corrected based on the first image as prior information. In some embodiments, the second imaging device may be the cone beam computed tomography (CBCT) device. The second projection data may be generated based on signals sampled by the detector of the CBCT device (e.g., the detector 112 of the imaging device 110 as illustrated in FIG. 1). The CBCT image may be used to provide position information during the IGRT. The CBCT projection data or the CBCT image may be used for in-vivo an electronic portal image device (EPID) based dose verification.

In some embodiments, the treatment isocenter of the first image (e.g., an MDCT image) may be well aligned with the machine isocenter of the second imaging device (e.g., a CBCT device), and the treatment isocenter of the first image and the isocenter of the second imaging device may be substantially the same. During generating the first projection data, the treatment isocenter of the first image may be set as a volume origin associated with the first projection data so that the volume origin associated with the first projection data coincides with the volume origin associated with the second projection data. Thus, time consuming calculation procedure including an image reconstruction (e.g., a first-pass reconstruction), three-dimensional image registration time and online forward projection time are get rid of while only two-dimensional registration is needed, which may significantly reduce the registration time and the computational cost of the registration.

In some embodiments, the first projection data or the plurality of first images may correspond to a first area of the subject. The first area may include an anatomical structure of the subject. The second projection data may correspond to a second area of the subject, and the first area may at least partially overlap with the second area in an overlapping area. In some embodiments, the first area may be substantially the same as the second area. The first area and the second area may include the same anatomical structure. The term "anatomical structure" in the present disclosure may refer to gas in the patient (e.g., air), liquid in the patient (e.g., water), solid in the patient (e.g., stone), one or more cells of the subject, one or more tissues of the subject, one or more organs of the subject, or any combination thereof, which are displayed in a plurality of images (e.g., the plurality of first images, or a plurality of second images which would be described elsewhere of the present disclosure, etc.) In some embodiments, the anatomical structure may be an anatomical structure of interest (ASI) of the subject. The term "anatomical structure of interest" (ASI) in the present disclosure may refer to a certain anatomical structure need to be tracked during the radiotherapy (e.g., the IGRT). In some embodiments, the ASI may need to be treated by the radiotherapy. In some embodiments, the ASI may be a cell, a tissue, an organ, or any combination thereof. In some embodiments, the ASI may be a tumor, or an organ with a tumor, or a tissue with a tumor. In some embodiments, the first projection data may be stored in the storage device 150. In some embodiments, the obtaining module 410 may acquire the second projection data from the imaging device 110 (e.g., a CBCT device) via the network 120. In some embodiments, the second projection data obtained by the imaging device 110 may be stored in the storage device 150.

The projection data determination module 420 may be configured to determine first projection data based on the plurality of first images. The plurality of first images or the first projection data may relate to the anatomical structure included in the plurality of first images.

The first projection data may be determined based on the plurality of first images via forward projection. In some embodiments, the correction of the scatter components may be performed in a projection domain or in an image domain. Merely by way of illustration, the present disclosure provides a method for correcting the scatter components in the projection domain. Projection data of the to-be-corrected image may include primary component and scatter component. The primary component may represent attenuation of an energy beam (e.g., an x-ray beam) through a subject. The scatter component may lead to scatter artifacts, and the primary component may be devoid of the scatter component. The first projection data of the plurality of first images (e.g., the MDCT images), due to advantages (e.g., much fewer scatter radiation signals) of the first imaging device (e.g., the MDCT device), may include the primary projection data without the scatter components.

As mentioned above, projection data (e.g., the first projection data, also referred as simulated projection data) of an image (e.g., the first image) may be determined based on the distribution function of linear attenuation coefficients $\mu(x, y)$. The distribution function of linear attenuation coefficients $\mu(x, y)$ may be determined based on pixel values of a plurality of pixels of the image (e.g., the first image). The distribution function of linear attenuation coefficients $\mu(x, y)$ may be related to one or more materials of an anatomical structure represented by the image, since linear attenuation coefficients for different materials or compositions are different. In some embodiments, the linear attenuation coefficients $\mu(x, y)$ may be determined based on one or more material categories corresponding to the one or more materials or compositions of the anatomical structure displayed in the image (e.g., lung tissue, brain tissue, muscle tissue, bone, fat, etc.).

The projection data (e.g., the first projection data) of the image (e.g., the first image) may also relate to an energy spectrum of the energy beam (e.g., the x-ray beam) of the second imaging device. The linear attenuation coefficients $\mu(x, y)$ of the subject may relate to a mass attenuation coefficient and the density of the material. The mass attenuation coefficient of a material may be a function of an energy level of the energy beam. For example, if the energy beam is a polychromatic beam (e.g., an x-ray beam with a range of energy spectrum), different components of the energy spectrum may be not attenuated uniformly when passing through the subject. The lower energy component of the polychromatic beam may be more easily attenuated when travelling through a dense part of the subject.

The projection data (e.g., the first projection data) of the image (e.g., the first image) may also relate to an image receptor energy response of second imaging device. The pixel value of projection data may be a function of an image receptor energy response. For example, when photons of different energies passing through the subject arrive the surface of image receptor, the contribution of different energies photon on the projection image is different as the conversion coefficient from photon to final electron varies at different energy range. For example, the image receptor energy response may be obtained via Monte Carlo simulation or calculated via experiments. As an exemplary embodiment, image receptor energy response is described in Chinese patent application No. 201811087948.X, and the contents of these applications are referenced herein and incorporated into this application.

The projection data registration module 430 may be configured to determine registered first projection data by registering the first projection data with the second projection data with respect to the overlapping area. In some embodiments, the projection data registration module 430 may obtain the first projection data and the second projection data from the storage device 150 via the network 120. The projection data registration module 430 may employ different registration methods to register the first projection data with the second projection data with respect to the overlapping area. Exemplary registration methods may include maximization of mutual information-based registration, surface-based registration, geometric moment-based registration, etc. When the first projection data is registered with the second projection data, the second projection data may be fixed as the target and the first projection data may be registered to the second projection data, or the first projection data may be fixed as the target and the second projection data may be registered to the first projection data, or a combination of both may be performed. Preferably the second projection data is fixed and the first projection data is registered to the second projection data. The registration may minimize a simulated error between the first projection data and the second projection data caused by anatomical structure. In some embodiments, the projection data registration module 430 is optional.

The scatter component determination module 440 may be configured to determine scatter component based on the registered first projection data and the second projection data. As a result of the registration, the scatter component may be due mainly to the scatter radiation data contained in the second projection data. The scatter component may represent a scatter distribution related to the second projection data. Most of the scatter artifacts result from low-frequency scatter components in the projection data. In some embodiments, the scatter components may be determined by subtracting the second projection data from the registered first projection data, then low-frequency filtering (also termed low-pass filtering) or smoothing may be applied to the subtraction result to determine the scatter components. In some embodiments, the scatter components may be determined by subtracting the registered first projection data from the second projection data, then low-frequency filtering or smoothing may be applied to the subtraction result to determine the scatter components. For example, a low-pass Gaussian filter may be applied to the scatter component without affecting the low-frequency primary components in the projection data. In some embodiments, the scatter components may need to be corrected due to non-perfect geometry alignment of the first imaging device and/or the second imaging device and respiratory movement of the subject.

The corrected projection data determination module 450 may be configured to determine corrected second projection data based on the scatter components and the second projection data. In some embodiments, the corrected projection data determination module 450 may obtain the scatter components and the second projection data from the storage device 150 via the network 120. The corrected projection data determination module 450 may determine the corrected second projection data by subtracting the scatter components from the second projection data. In some embodiments, the corrected second projection data may be determined by subtracting the corrected scatter component from the second projection data. Thus, the corrected second projection data may be scatter-free. In some embodiments, the corrected second projection data may be stored in the storage device 150.

In some embodiments, one or more modules illustrated in FIG. 4 may be implemented in at least part of the exemplary imaging system 100 as illustrated in FIG. 1. For example, the obtaining module 410, the projection data determination module 420, the projection data registration module 430, the scatter component determination module 440, the corrected projection data determination module 450 may be integrated into a console (not shown) with a user interface component. Via the console, a user may set parameters for scanning a subject, controlling imaging processes, controlling parameters for reconstruction of an image, viewing reconstructed images, provide an instruction regarding the delivery of a treatment plan or a portion thereof, etc. In some embodiments, the console may be implemented via the processing device 140 and/or the terminal(s) 130.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. Merely by way of example, the processing device 140 may include one or more other modules. However, those variations and modifications also fall within the scope of the present disclosure.

Figure 5:
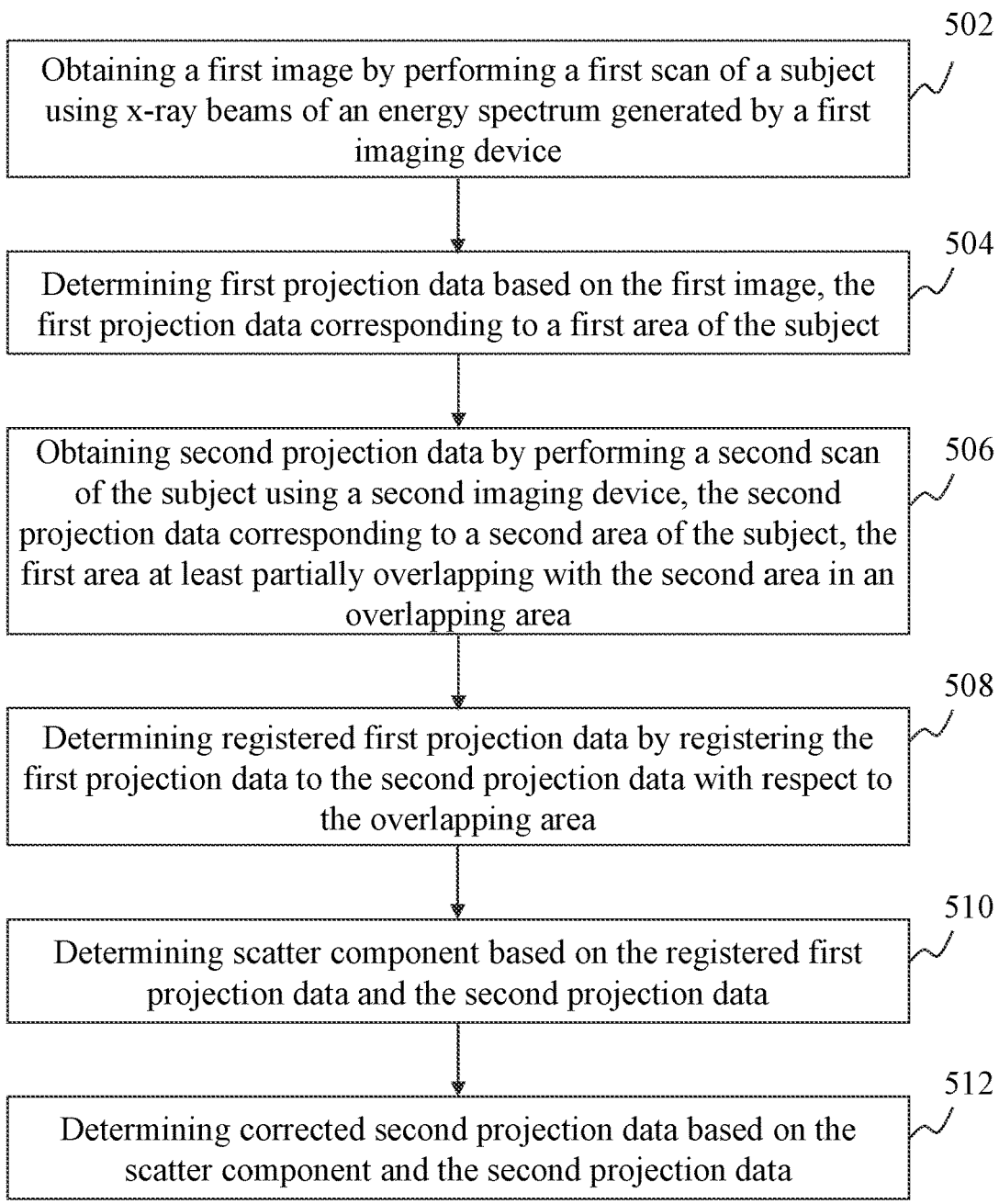
FIG. 5 is a flowchart illustrating an exemplary process for reconstructing an image based on corrected projection data according to some embodiments of the present disclosure.

FIG. 5 illustrates a flowchart illustrating an exemplary process for correcting scatter component in projection data based on prior information according to some embodiments of the present disclosure. In some embodiments, at least part of process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 502, a plurality of first images may be obtained. Operation 502 may be performed by the obtaining module 410. The plurality of the first images may be acquired by performing a first scan of a subject using energy beams generated by a first imaging device. A first image volume may be included in the plurality of first images. An image volume may include a plurality of voxels of the subject. A first image as used in the present disclosure may refer to a reference image with relatively fewer scatter artifacts than a to-be-corrected image, and the scatter artifacts of the to-be-corrected image may be corrected based on the first image as prior information. The first image may include a CT image, an EPID image, a fluoroscopy image, an ultrasound image, or a PET image, etc. Merely by way of example with reference to a radiation treatment, the first image may be a planning image according to which a treatment plan is made. The treatment plan may describe how a radiation treatment is performed on a subject (e.g., patient). Merely by way of example, the first imaging device may be a multi-detector computed tomography (MDCT) device, and the first scan is an MDCT scan. With fewer scatter radiation regions than a CBCT device, a MDCT scan may be performed for radiation treatment planning. For example, in the image-guided radiation therapy (IGRT), MDCT, because of the high image quality it provides, may be used to generate a planning image for treatment plan determination, and CBCT, because of the relative faithful accuracy and a shorter imaging time it provides, may be used to provide position information during the performance of IGRT. According to some embodiments of the present disclosure, the MDCT image (e.g., the first image) may serve as prior information to correct the CBCT image with respect to the same subject.

In some embodiments, the first image may relate to a treatment isocenter assigned by doctors or physicists. After coarse positioning, the treatment isocenter of the first image may be close to a machine isocenter of the second imaging device at which the energy beams emitted from different gantry angles intersect.

In some embodiments, the first image may be generated by the MDCT imaging device in advance, and stored in the storage device 150. In some embodiments, the obtaining module 410 may acquire the first image from the storage device 150 via, e.g., the network 120. In some embodiments, the first image may generally refer to any reconstructed image of the subject with reduced or no scattered radiation signals.

In 504, first projection data may be determined based on the plurality of first images. In some embodiments, the first projection data may be determined by the projection data determination module 420. In some embodiments, the first projection data or the plurality of first images may correspond to a first area of the subject. The first area may include an anatomical structure of the subject. The plurality of first images or the first projection data may relate to the anatomical structure represented in the plurality of first images. The term "anatomical structure" in the present disclosure may refer to gas in the subject (e.g., air), liquid in the subject (e.g., water), solid in the subject (e.g., stone), one or more cells of the subject, one or more tissues of the subject, one or more organs of the subject, or a portion thereof, or any combination thereof, which is/are represented in a plurality of images (e.g., the plurality of first images, or a plurality of second images which are described elsewhere in the present disclosure, etc.). The subject may include a patient. In some embodiments, the anatomical structure may be an anatomical structure of interest (ASI) of the subject. The term "anatomical structure of interest" (ASI) in the present disclosure may refer to a certain anatomical structure that needs to be tracked during a radiotherapy (e.g., the IGRT). In some embodiments, the ASI may need to be treated by the radiotherapy. In some embodiments, the ASI may be a cell, a tissue, an organ, or a portion thereof, or any combination thereof. In some embodiments, the ASI may be a tumor, or an organ with a tumor, or a tissue with a tumor. In some embodiments, the first projection data may be stored in the storage device 150.

The first projection data may be determined based on the plurality of first images via forward projection. In some embodiments, the correction of the scatter artifacts may be performed in a projection domain or in an image domain. Merely by way of illustration, the present disclosure provides a method for correcting the scatter artifacts via the projection domain. Projection data of the to-be-corrected image may include primary components and scatter components. The scatter components may lead to the scatter artifacts, and in the primary projection data, the scatter components may be removed or reduced. The first projection data of the plurality of first images (e.g., the MDCT images), due to advantages (e.g., much fewer scatter radiation signals) of the first imaging device (e.g., the MDCT device), may include the primary projection data with reduced or no scatter components.

Merely by way of illustration, the first projection data may be determined based on the plurality of first images by a forward projection technique. Exemplary forward projection techniques may include ray-driven techniques and distance-driven techniques. In some embodiments, Siddon's ray tracing algorithm may be used to perform the forward projection of the first image (e.g., the MDCT image). Other ray-driven techniques may include, as an example in the 2D image case, calculating the line integrals by performing linear interpolation between two pixels for each row or column intersected by a projection line, using the nearest-neighbor or no interpolation spherical basis functions, and natural pixels. In the 3D image case, for example, trilinear interpolation may be analogously used to interpolate between voxels.

Figure 9:
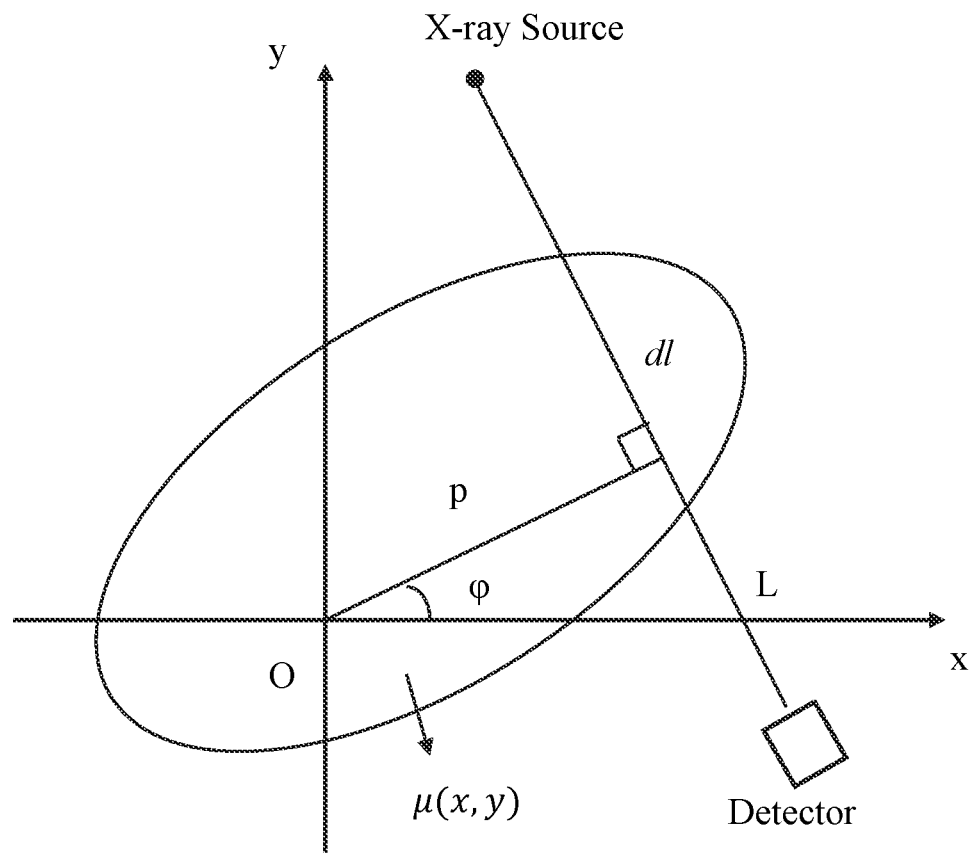
FIG. 9 is a schematic diagram illustrating a section of a subject through which X-ray beams pass.

As used herein, projection data may represent attenuation of an energy beam (e.g., an x-ray beam) through a subject. The projection data may be a sum or line integrals of linear attenuation coefficient(s) along a certain direction of the energy beam. Taking the x-ray beam as an example, as shown in FIG. 9, the x-y plane may be a section of the subject that the X-ray beams pass through. Line L may be a path of an energy beam (e.g., an X-ray beam) passing through the section of the subject. The complementary angle of angle φ may be the angle between the X-ray beam and the x axis. Assuming that the intensity of the energy beam source (taking the X-ray beam as an example, the energy beam source may be the scanning source 115 of the imaging device 110 as illustrated in FIG. 1) is $I_0$, the intensity of the X-ray beams after passing through the subject is I, and the subject is composed of a uniform material with a linear attenuation coefficient μ, $I_0$ and I may follow the Beer's law. When the subject is composed of a non-uniform material, assuming that μ(x, y) is a distribution function of linear attenuation coefficients of the section of the subject, the projection data I may follow an equation expressed as follows:

$$I = I_0 \exp(-\int_L \mu(x, y) dl), \quad (1)$$

where $I_0$ denotes projection values in the air without any object. If energy spectrum and image receptor energy response is taken into consideration, the above equation can be expressed as follows:

$$I=I_0\Sigma_k\varphi_k \exp(\Sigma_l\mu(k,l)dl)\eta_k, \qquad (2)$$

where $\varphi_k$ are weight of energy spectrum at k bin, $\eta_k$ are weight of image receptor energy response at k bin, $\mu(k,l)$ is a distribution function of linear attenuation coefficients of the section of the subject at k bin.

As mentioned above, projection data (e.g., the first projection data) of an image (e.g., the first image) may be determined based on the distribution function of linear attenuation coefficients $\mu(x, y)$. The distribution function of linear attenuation coefficients $\mu(x, y)$ may be determined based on pixel values of a plurality of pixels of the image (e.g., the first image). The distribution function of linear attenuation coefficients $\mu(x, y)$ may relate to one or more materials or compositions of an anatomical structure represented by the image (e.g., a material distribution), since linear attenuation coefficients for different materials or compositions are different. In some embodiments, the linear attenuation coefficients $\mu(x, y)$ may be determined based on one or more material (or composition) categories corresponding to the one or more materials or compositions of the anatomical structure displayed in the image. More descriptions related to the determination of the linear attenuation coefficients $\mu(x, y)$ based on the material (or composition) category (e.g., a material distribution) may be found elsewhere in the present disclosure. See, e.g., FIG. 6 and the descriptions thereof The projection data (e.g., the first projection data) of the image (e.g., the first image) may also relate to an energy level or spectrum of the energy beam (e.g., the X-ray beam). The linear attenuation coefficients $\mu(x, y)$ of the subject may relate to a mass attenuation coefficient and the density of the material. The mass attenuation coefficient of a material (or composition) may be a function of the energy level of an energy beam. For example, if the energy beam is a polychromatic beam (e.g., an X-ray beam whose energy levels fall within an energy spectrum), components of different energy levels of the energy spectrum may be attenuated non-uniformly when passing through the subject. The lower energy component of the polychromatic beam may be attenuated more when travelling through a dense part (a part with a higher density) of the subject. More descriptions related to the determination of the linear attenuation coefficients $\mu(x, y)$ based on the energy spectrum of the energy beam may be found elsewhere in the present disclosure. See, e.g., FIG. 7 and descriptions thereof In 506, second projection data may be obtained. Operation 506 may be performed by the obtaining module 410. Second projection data may be acquired by performing a second scan of the subject using a second imaging device. A plurality of second images may be reconstructed based on the second projection data. A second image in the present disclosure may refer to the to-be-corrected image with relatively more scatter artifacts than the first image(s) because the projection data of the to-be-corrected image may include more scatter components than the first projection data as mentioned elsewhere in the present disclosure, and the scatter artifacts of the second image(s) may be corrected based on the first image(s) used as prior information. The second image may include a CT image, an EPID image, a fluoroscopy image, an ultrasound image, a PET image, or an MRI image, etc. In some embodiments, the second imaging device may be a cone beam computed tomography (CBCT) device. The second projection data may be sampled by the detector of the CBCT device (e.g., the detector 112 of the imaging device 110 as illustrated in FIG. 1). The CBCT image may be used to provide positioning information during IGRT.

The second projection data may relate to a machine isocenter of the second imaging device. The machine isocenter of the second imaging device may be a point at which the energy beams emitted from different gantry angles intersect. In some embodiments, the machine isocenter of the second imaging device and the treatment isocenter of the first image may be well aligned and substantially the same. Thus, the volume origin associated with the first projection data and the volume origin associated with the second projection data may be substantially the same.

The second projection data may correspond to a second area of the subject, and the first area may at least partially overlap with the second area in an overlapping area. In some embodiments, the first area may be substantially the same as the second area. The first area and the second area may include the same anatomical structure (e.g., the ASI). In some embodiments, the obtaining module 410 may acquire the second projection data from the imaging device 110 (e.g., a CBCT device) via the network 120. In some embodiments, the second projection data obtained by the imaging device 110 may be stored in the storage device 150.

In 508, registration of the first projection data with the second projection data may be performed. The registration may be performed with respect to the overlapping area. Operation 508 may be performed by the projection data registration module 430. In some embodiments, the projection data registration module 430 may retrieve the first projection data and the second projection data from the storage device 150 via, e.g., the network 120. The projection data registration module 430 may employ different registration techniques to register the first projection data with the second projection data with respect to the overlapping area. Exemplary registration techniques may include maximization of mutual information-based registration, surface-based registration, geometric moment-based registration, etc. To perform the registration, the second projection data may be fixed as the reference and the first projection data may be registered with respect to the second projection data to obtain registered first projection data, and alternatively the first projection data may be fixed as the reference and the second projection data may be registered with respect to the first projection data to obtain registered second projection data, or a combination thereof. In some embodiments, the second projection data is fixed as the reference and the first projection data is registered to the second projection data. The registration may reduce or minimize a simulated error between the first projection data and the second projection data caused by the anatomical structure. In some embodiments, the treatment isocenter of the first image and the machine isocenter of the second imaging device may be substantially the same, thus operation 508 may be optional.

In some embodiments, the treatment isocenter of the first image (e.g., an MDCT image) may be well aligned with the machine isocenter of the second imaging device (e.g., a CBCT device), the treatment isocenter of the first image and the machine isocenter of the second imaging device may be substantially the same. For instance, the distance between the treatment isocenter of the first image and the machine isocenter of the second imaging device may be smaller than a threshold, e.g., 1 centimeters, 0.5 millimeters, etc. During generating the first projection data, the treatment isocenter of the first image may be set as a volume origin associated with the first projection data so that the volume origin associated with the first projection data coincides with the volume origin associated with the second projection data. Thus, time consuming calculation procedures including a first-pass reconstruction, three-dimensional image registration time and online forward projection time are avoided while only two-dimensional registration of projection data is needed, which may significantly reduce the registration time and the computational cost of the registration. In some embodiments, the registered first projection data may be stored in the storage device 150.

In 510, scatter component may be determined based on the first projection data and the second projection data after their registration. Merely by way of example, the first projection data may be registered with respect to the second projection data using the second projection data as the reference. It is understood that the scatter component may also be determined based on registration in which the second projection data are registered with respect to the first projection data using the first projection data as the reference. Operation 510 may be performed by the scatter component determination module 440. As a result of the registration in operation 508, the scatter component may be due mainly to the scatter radiation data contained in the second projection data. The scatter component may represent a scatter distribution in the second projection data. Most of the scatter artifacts may stem from low-frequency scatter components in the projection data. In some embodiments, the scatter components may be determined by subtracting the second projection data from the registered first projection data, then low-frequency filtering or smoothing may be applied to the subtraction result to determine the scatter components. In some embodiments, the scatter components may be determined by subtracting the registered first projection data from the second projection data, then low-frequency filtering or smoothing may be applied to the subtraction result to determine the scatter components. For example, a low-pass Gaussian filter may be applied to the scatter component without affecting the low-frequency scatter components in the projection data. In some embodiments, the scatter component may need to be corrected due to, e.g., a geometry mis-alignment of the first imaging device with the second imaging device, respiratory movement of the subject, or the like, or a combination thereof. More descriptions related to the correction of the scatter component may be found elsewhere in the present disclosure. See, e.g., FIG. 8 and the descriptions thereof. In some embodiments, the scatter component may be determined by the scatter component determination module 440 and/or stored in the storage device 150.

In 512, corrected second projection data may be determined based on the scatter component and the second projection data. Operation 512 may be performed by the corrected projection data determination module 450. In some embodiments, the corrected projection data determination module 450 may retrieve the scatter component and the second projection data from the storage device 150 via, e.g., the network 120. The corrected projection data determination module 450 may determine the corrected second projection data by subtracting the scatter component from the second projection data. In some embodiments, the corrected second projection data may be determined by subtracting the scatter component from the second projection data. Thus, the corrected second projection data may be substantially scatter-free. In some embodiments, the corrected second projection data may be stored in the storage device 150.

In some embodiments, a corrected image may be reconstructed based on the corrected second projection data. In some embodiments, the corrected second projection data may be retrieved from the storage device 150. Different reconstruction algorithms may be employed to reconstruct the corrected image based on the corrected second projection data of the subject. Exemplary reconstruction algorithms may include a direct matrix inversion algorithm, an iterative algorithm, a Fourier reconstruction algorithm, a backprojection algorithm, a filtered backprojection algorithm, etc.

It should be noted that the above descriptions of the process 500 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 500 may include one or more other operations. However, those variations and modifications also fall within the scope of the present disclosure.

Figure 6:
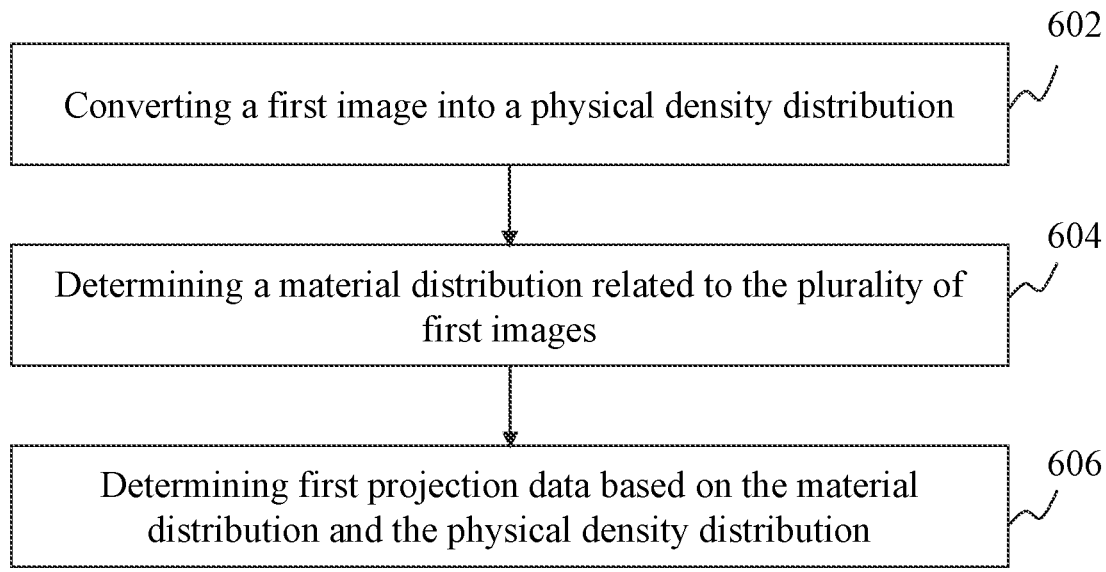
FIG. 6 illustrates a flowchart illustrating an exemplary process for determining projection data based on an image according to some embodiments of the present disclosure.

FIG. 6 illustrates a flowchart illustrating an exemplary process for determining the first projection data based on the first image according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. Considering that different material (or composition) categories may have inherent different linear attenuation coefficients for an energy beam (e.g., the X-ray beam), material (or composition) categories (e.g., the material distribution) may be taken into consideration when the first projection data are determined based on the first image.

In 602, a physical density distribution related to the plurality of first images may be determined based on the plurality of first images. Operation 602 may be performed by the projection data determination module 420. The physical density distribution may represent a density distribution of the anatomical structure represented by the plurality of first images. In some embodiments, the density distribution related to the plurality of first images may be obtained directly if the first scan device is a dual energy CT device. In some embodiments, the determination module 420 may determine the physical density distribution related to a first image based on the first image. The first image may include a plurality of pixels. A pixel may include one or more pixel values. The pixel value may refer to the value of a property of the pixel. For instance, the pixel value may refer to a CT number of the pixel, a luminance value of the pixel, the grey value of the pixel, the color or RGB value of the pixel, the saturation value of the pixel, or the like, or a combination thereof. When the first image is a CT image, the pixel value (e.g., the CT number) may reflect the extent of absorption of the energy beam (e.g., the x-ray beam) by the anatomical structure of the subject (e.g., a patient) reflected by the first image. For instance, the first image may reflect a CT number distribution of the anatomical structure of the subject. The conversion from the CT number distribution to the physical density distribution may be obtained by searching a CT number-to-physical density map. The CT number-to-physical density map may record a correspondence relation between the CT number of a pixel and a physical density of the pixel corresponding to a point in the anatomical structure. For example, if a pixel of the first image has a CT number A, the determination module 420 may determine the physical density of the pixel as B according to the CT number-to-physical density map. In some embodiments, the CT number-to-physical density map may be obtained by scanning an electron density phantom using the first imaging device.

In 604, a material distribution related to the plurality of first images may be determined. Operation 604 may be performed by the projection data determination module 420. In some embodiments, the material distribution related to the plurality of first images may be obtained directly if the first scan device is a dual energy CT device. In some embodiments, the projection data determination module 420 may segment a first image into one or more sections based on the physical density distribution or the CT numbers of the plurality of first images, in which each section corresponds to a material (or composition) category, and determine the material distribution based on the one or more sections. The one or more sections may include an air section, a lung tissue section, a soft tissue section, and a hard tissue segment. For example, the projection data determination module 420 may segment a plurality of pixels of the first image into the air section if the physical densities and/or the CT numbers of the plurality of pixels is within a predetermined range.

In 606, first projection data may be determined based on the material distribution and the physical density distribution. Operation 606 may be performed by the projection data determination module 420. Because the linear attenuation coefficient of the subject of a material (or composition) category for a given photon of the energy beam (e.g., X-ray) is proportional to the physical density value of the subject in the material (or composition) category, the physical density distribution may be proportional to the distribution of linear attenuation coefficients. The distribution function of linear attenuation coefficients $\mu(x, y)$ may be determined based on the one or more sections or the corresponding material (or composition) categories (e.g., the material distribution) and the physical density distribution, and the first projection data may then be determined.

As mentioned above, the projection data (e.g., the first projection data) of the image (e.g., the first image) may also relate to an energy spectrum of the energy beam (e.g., the X-ray beam). The linear attenuation coefficients $\mu(x, y)$ of an object may relate to a mass attenuation coefficient and the density of the material. The mass attenuation coefficient of a material (or composition) may be a function of the energy level(s) of the energy beam. For example, if the energy beam is a polychromatic beam (e.g., an X-ray beam whose energy levels fall within an energy spectrum), components of different energy levels of the energy spectrum may be attenuated non-uniformly when passing through the subject. The lower energy component of the polychromatic beam may be more easily attenuated when travelling through a dense part of the subject. More descriptions related to determining the linear attenuation coefficients $\mu(x, y)$ based on the energy spectrum of the energy beam may be found elsewhere in the present disclosure. See, e.g., FIG. 7 and the descriptions thereof.

It should be noted that the above descriptions of the process 600 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 600 may include one or more other operations. However, those variations and modifications also fall within the scope of the present disclosure.

Figure 7:
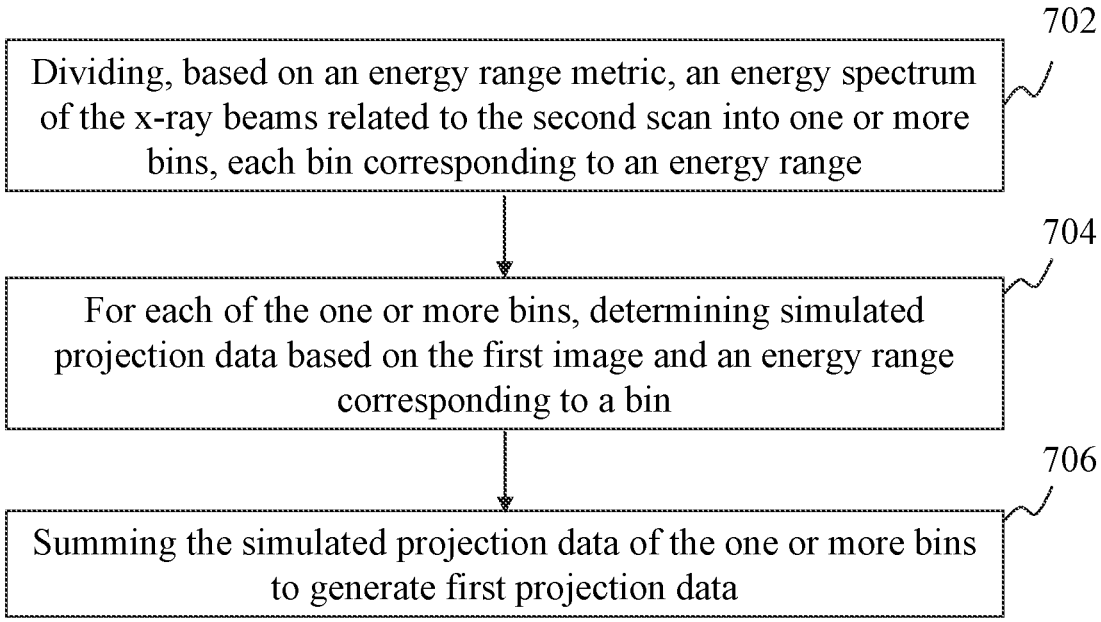
FIG. 7 illustrates a flowchart illustrating an exemplary process for determining projection data based on an image according to some embodiments of the present disclosure.

FIG. 7 illustrates a flowchart illustrating an exemplary process for determining the first projection data based on the first image according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 702, based on an energy-range-based metric, an energy spectrum of the X-ray beam related to the second scan may be divided into one or more bins. Operation 702 may be performed by the projection data determination module 420. Each bin may correspond to an energy range. In some embodiments, the energy spectrum of the X-ray beams related to the second scan may be divided into one or more regular (e.g., uniformly distributed) bins. For example, an energy range of the energy spectrum of the x-ray beams may be from 1 keV to 100 keV. The energy spectrum of the x-ray beams may be divided into 20 regular bins. Bin 1 may correspond to an energy range from 1 keV to 5 keV, Bin 2 may correspond to an energy range from 5 keV to 10 keV, . . . , and Bin 20 may correspond to an energy range from 95 keV to 100 keV. Under this situation, a same weight or different weights may be assigned to the one or more bins. In some embodiments, the weight may be assigned based on the prevalence of photons in each energy bin within the beam.

In some embodiments, the energy spectrum of the x-ray beams related to the second scan may be divided into one or more irregular (e.g., non-uniformly distributed) bins. For instance, an energy range of the energy spectrum of the x-ray beams may be from 0 keV to 120 keV. The energy spectrum of the x-ray beams corresponding to an energy range from 0 to 80 keV may be divided into 8 regular bins, and each bin may correspond to an energy range, such as 0 to 10 keV, 10 keV to 20 keV, . . . , 70 keV to 80 keV. The energy spectrum of the x-ray beams corresponding to an energy range from 80 to 120 KeV may be divided into 8 regular bins, and each bin may correspond to an energy range, such as 80 keV to 85 keV, 85 keV to 90 keV, . . . , 115 keV to 120 keV. Under this situation, a same weight or different weights may be assigned to the one or more bins. For instance, all of the 16 energy bins may be equally weighted, and the assigned weight may be $1/16$. In some embodiments, the projection data determination module 420 may divide the energy spectrum of the x-ray beams related to the second scan into one or more bins based on an energy range metric, each bin may correspond to an energy range. The projection data determination module 420 may employ any suitable manner to divide the energy spectrum of the x-ray beams related to the first image into one or more bins. The above description is merely provided for illustration purposes, and it is not intended to limit the scope of the present disclosure.

The width of the energy bins, may, for example, be divided according to the relative occurrence of x-ray energies. For example, the cumulative energy spectral distribution function may be determined by integrating the energy spectrum with respect to energy. If, for example, 10 bins are to be created, 9 equi-spaced ordinates may be selected from the cumulative distribution function, i.e. 0.1, 0.2, 0.3, 0.4, 0.5, 0.6, 0.7, 0.8, 0.9. By means of inverse look-up of the cumulative distribution function abscissa points, this yields 9 energy bin limits, with each bin containing approximately or exactly one tenth of the x-ray photons present in the beam. In such cases, substantially equal weights may be applied to each bin when forming a polychromatic projection from monochromatic projection components. Accordingly, the image receptor energy response may be divided in the same method. If, for example, the width of detector response's energy bins are identical to those of energy spectrum. As an exemplary embodiment, image receptor energy response is described in Chinese patent application No. 201811087948.X, and the contents of these applications are referenced herein and incorporated into this application.

In 704, for each of the one or more bins, simulated projection data may be determined based on a first image of the plurality of first images and an energy range corresponding to a bin. The linear attenuation coefficient for the particular material traversed by the x-ray beams, at an energy representative of the particular energy bin, may be determined in Operation 704. Operation 704 may be performed by the projection data determination module 420. In some embodiments, the projection data determination module 420 may determine the simulated projection data based on the first image and an energy range corresponding to a bin. The simulated projection data corresponding to a bin k may be determined based on following equation:

$$I_k = I_0 \varphi_k \exp(\Sigma_l \mu(k,l) dl) \eta_k, \quad (3)$$

where $\varphi_k$ are weight of energy spectrum at k bin, $\eta_k$ are weight of image receptor energy response at k bin, $\mu(k,l)$ is a distribution function of linear attenuation coefficients of the section of the subject at k bin.

If the subject is composed of a uniform material or composition with a linear attenuation coefficient $\mu_k$, the simulated projection data determination unit 540 may determine the simulated projection data based on the first image and an energy range corresponding to a bin according to equation (2) or equation (3).

In some embodiments, the subject is made of a non-uniform material or composition, the simulated projection data determination unit 540 may determine the simulated projection data taking material or composition categories (e.g., the material distribution) and energy spectrum of the x-ray beams into consideration. With reference to process 600 illustrated in FIG. 6, the first image may be segmented into one or more sections, and the physical density distribution corresponding to the first image may be obtained by searching the CT number-to-physical density map. For each of the one or more bins, the simulated projection data determination unit 540 may determine, based on the one or more sections or corresponding material or composition categories and the energy range corresponding to the bin, a mass attenuation coefficient matrix for the plurality of voxels corresponding to the bin. The mass attenuation coefficient matrix for the plurality of voxels corresponding to the bin may be obtained by searching a lookup table or mass attenuation coefficient table. The lookup table may be constructed according to a relationship between the mass attenuation coefficients and X-ray beam energy levels, and the atomic number of the material or composition. The mass attenuation coefficient table of different materials or compositions can be made. The simulated projection data determination unit 540 may determine, based on the mass attenuation coefficient matrix and the physical density distribution, a linear attenuation coefficient matrix corresponding to the bin. The linear attenuation coefficient matrix corresponding to the bin may be obtained by multiplication of the mass attenuation coefficient matrix and the corresponding material physical densities. The simulated projection data determination unit 540 may determine, based on the linear attenuation coefficient matrix, the simulated projection data of the bin.

In 706, the simulated projection data of the one or more bins may be summed to generate first projection data. Operation 706 may be performed by the projection data determination module 420. In some embodiments, the first projection data determination unit 550 may sum the simulated projection data of the one or more bins to generate first projection data.

It should be noted that the above descriptions of the process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 700 may include one or more other operations. However, those variations and modifications also fall within the scope of the present disclosure.

Figure 8:
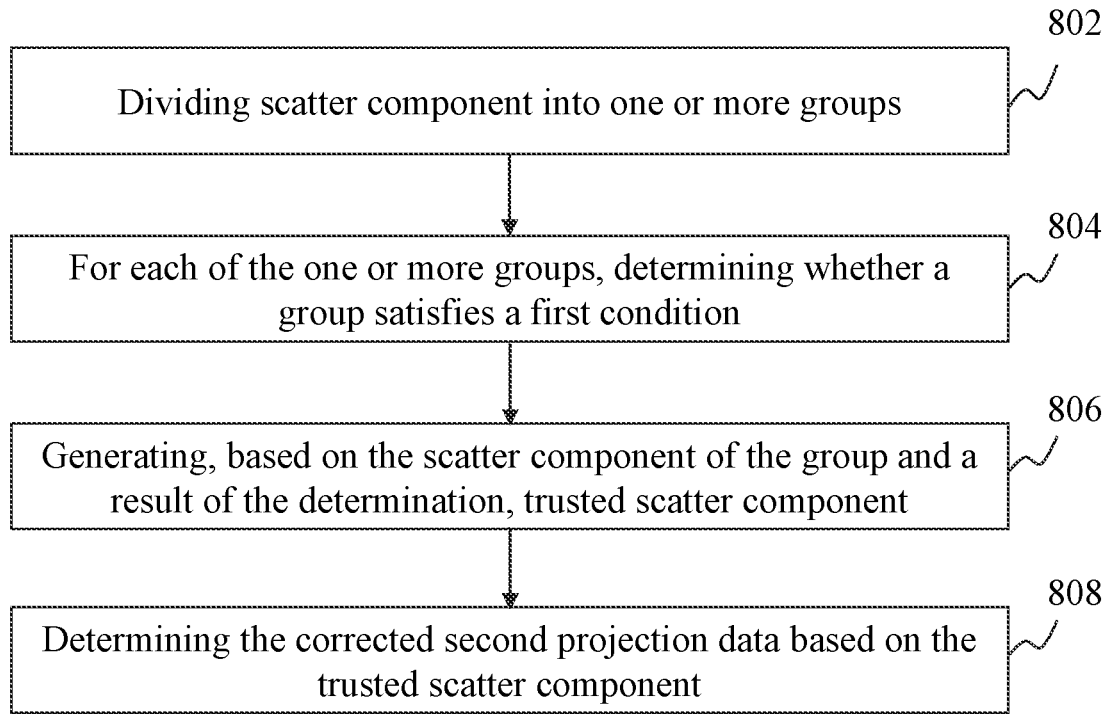
FIG. 8 illustrates a flowchart illustrating an exemplary process for determining corrected projection data based on scatter component according to some embodiments of the present disclosure.

FIG. 8 illustrates a flowchart illustrating an exemplary process for correcting scatter component according to some embodiments of the present disclosure. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, scatter component may be divided into one or more groups of projection data. Operation 802 may be performed by the corrected projection data determination module 450. The scatter component may be obtained based on the first projection data and the second projection data after their registration. For instance, the scatter component may be obtained by subtracting registered first projection data from the second projection data by low-frequency filtering or smoothing. More descriptions related to the determination of the scatter component may be found elsewhere in the present disclosure (e.g., operation 510 and the description thereof). Due to, e.g., a geometry mis-alignment of the first imaging device and/or the second imaging device, respiratory movement of the subject, etc., some portion of the scatter component may fail to faithfully represent an actual scatter distribution. In some embodiments, the corrected projection data determination module 450 may divide the scatter component into one or more groups to determine which group(s) of projection data precisely represent the scatter distribution, and untrusted group(s) of projection data may be removed from the scatter component. In some embodiments, the first projection data and the second projection data may also be divided into the one or more groups corresponding to the scatter component, that is, the scatter component in a group is determined based on the first projection data in the group and the second projection data in the group. For example, the corrected projection data determination module 450 may divide the scatter component into one or more groups based on the sections or corresponding material (or composition) categories, and the scatter component corresponding to the same material (or composition) category may be assigned to a group. As another example, the corrected projection data determination module 450 may divide the scatter component into one or more groups based on different regions (e.g., an edge region, a low-intensity-gradient region, a high-intensity-gradient region, etc.) The scatter component corresponding to the same region may be assigned to a group.

In 804, for each of the one or more groups, a determination may be made as to whether projection data of the group satisfies a first condition. Operation 804 may be performed by the corrected projection data determination module 450. In some embodiments, the corrected projection data determination module 450 may determine whether a group of projection data satisfies a first condition. A group of projection data that satisfies the first condition may be considered as trusted projection data that is deemed to precisely represent the scatter distribution. A group of projection data that do not satisfy the first condition may be considered as untrusted projection data that is deemed to fail to faithfully represent actual scatter distribution. In some embodiments, the first condition may be that a ratio of a sum of the registered first projection data in a group and the scatter component in the group to the second projection data in the group is within a certain range. For instance, the certain range may be [0.91, 1]. In some embodiments, the scatter component in the group may be positive and lower than a first threshold. Usually, the scatter component stemming from scatter may be positive. If the scatter component exceeds the first threshold, the scatter component in the group may result from a geometry mis-alignment of the first imaging device and/or the second imaging device, the influence of air region in the second image, etc., instead of scatter. The first condition may also be that the gradient of the scatter component in the group is lower than a second threshold. If the gradient of the scatter component in the group exceeds the second threshold, the scatter component in the group may result from a contour of the subject (a body edge of the subject) in the second image or the respiratory movement of the subject, instead of the scatter. In some embodiments, if scatter component in a group that satisfies all of the above mentioned first conditions, the scatter component in the group may be considered trusted data.

In 806, trusted scatter component may be generated based on the scatter component of the group and a result of the determination. Operation 806 may be performed by the corrected projection data determination module 450. In some embodiments, the corrected projection data determination module 450 may designate the scatter component of the group that satisfies any one of or combination of or all of the above mentioned first conditions as the trusted scatter component. The trusted scatter component may be determined by removing all the untrusted projection data of the one or more groups from the scatter component.

In 808, the corrected second projection data may be determined based on the trusted scatter component. The removal of the untrusted projection data from the scatter component may lead to the existence of one or more blank portions of the trusted scatter component compared to the scatter component, and thus the one or more blank portions of the trusted scatter component may be complemented to determine a complete scatter distribution. The corrected second projection data may be determined by complementing the one or more blank portions of the trusted scatter component. In some embodiments, the one or more blank portions may be complemented based on a scatter kernel technique, such as a scatter kernel superposition technique or a Monte Carlo technique, etc. For example, the corrected projection data determination module 450 may determine one or more areas in the second image corresponding to the one or more blank portions and determine scatter components corresponding to the one or more blank portions via scatter kernels. The scatter kernels may include a transfer function that relates to an energy beam fluence at a point within the subject and a scatter distribution of the point within the subject. In some embodiments, the one or more blank portions may be complemented based on an extrapolation technique, such as a median filter technique, a Gaussian filter technique, etc. For example, pixel values of the one or more blank portions may be first set to zero. Then, a median filter (e.g., a 44×44-pixel median filter) may be applied to the trusted scatter component. Finally, a Gaussian filter (e.g., a 51×51-pixel Gaussian filter with an 8-pixel standard deviation, or a 51×51-pixel Gaussian filter with a 20-pixel standard deviation) may be applied to the trusted scatter component. After the one or more blank portions of the trusted scatter component are complemented, the trusted scatter component may be used to determine the corrected second projection data according to some embodiments of the present disclosure (e.g., operation 510 and the description thereof).

It should be noted that the above descriptions of the process 800 are provided for the purposes of illustration, and are not intended to limit the scope of the present disclosure. For persons having ordinary skills in the art, various modifications and changes in the forms and details of the application of the above method and system may occur without departing from the principles of the present disclosure. In some embodiments, the process 800 may include one or more other operations. However, those variations and modifications also fall within the scope of the present disclosure.

Figure 10:
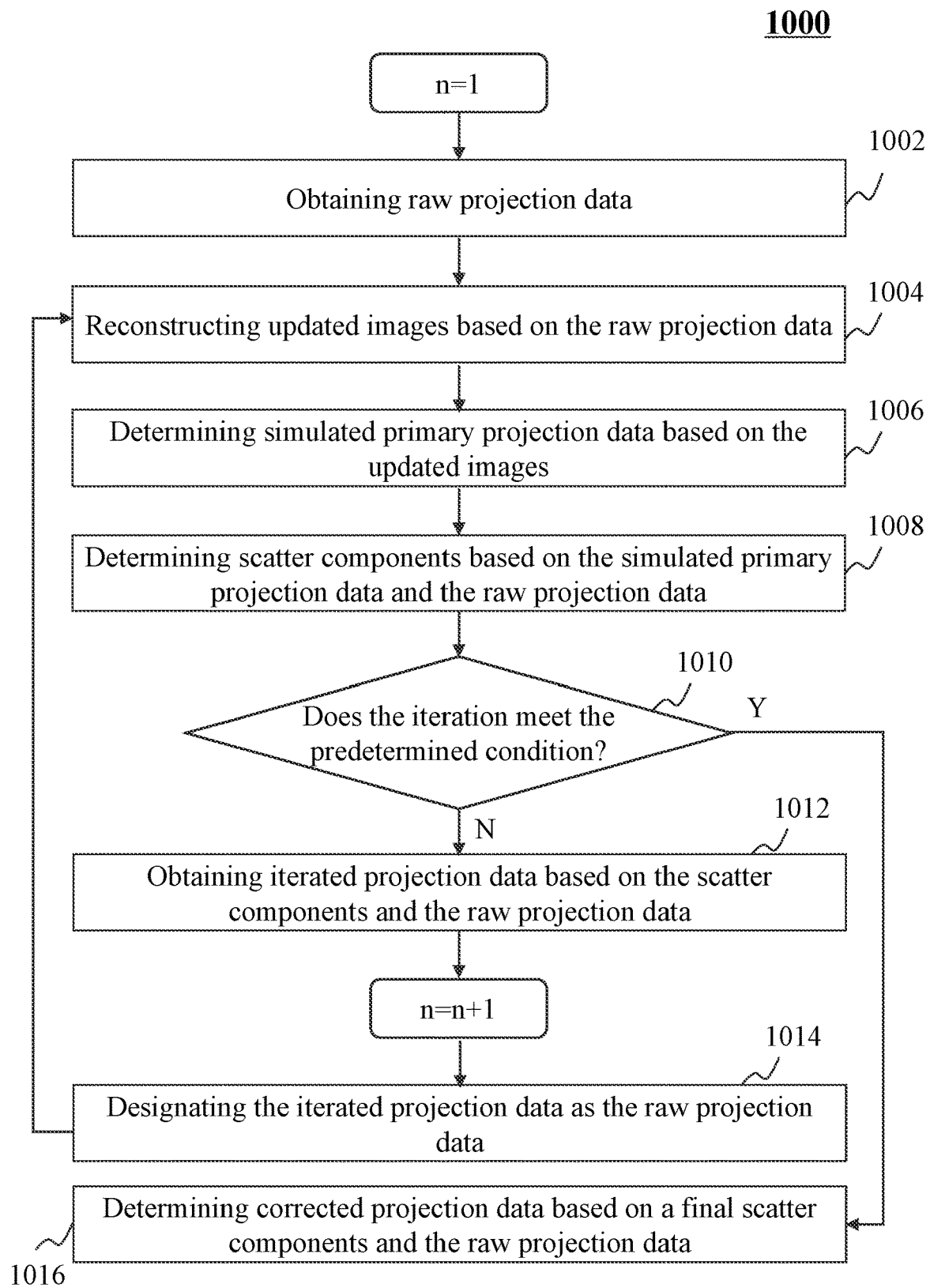
FIG. 10 is a flowchart illustrating an exemplary process for reconstructing an image based on raw projection data according to some embodiments of the present disclosure.

FIG. 10 is a flowchart illustrating an exemplary process for reconstructing an image based on raw projection data according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

When the prior information (e.g., the MDCT image) is not available, the scatter components of projection data may be corrected by following iterative operations until the iteration meets a predetermined condition (e.g., desired accuracy is achieved, convergence is achieved, iteration number exceeds default threshold value, etc.).

For the first iteration, the iteration number n may be equal to 1.

In 1002, raw projection data may be obtained. Operation 1002 may be performed by the obtaining module 410. Raw projection data may be acquired by performing a scan of the subject using a second imaging device. In some embodiments, the second imaging device may be a cone beam computed tomography (CBCT) device. The raw projection data may be sampled by the detector of the CBCT device (e.g., the detector 112 of the imaging device 110 as illustrated in FIG. 1). As used herein, the raw projection data may refer to to-be-corrected projection data with relatively more scatter artifacts. In some embodiments, the raw projection data may be stored in the storage device 150.

In 1004, updated images may be reconstructed based on the raw projection data. Operation 1004 may be performed by the scatter components determination module 440. Different reconstruction algorithms may be employed to reconstruct the updated images based on the raw projection data. Exemplary reconstruction algorithms may include a direct matrix inversion algorithm, an iterative algorithm, a Fourier reconstruction algorithm, a backprojection algorithm, a filtered backprojection algorithm, etc.

In 1006, simulated primary projection data may be determined based on the updated images. Operation 1006 may be performed by the scatter components determination module 440. In some embodiments, the simulated primary projection data may be determined based on the updated images via forward projection. More details about the forward projection may be found in FIG. 5, and descriptions thereof In 1008, scatter components may be determined based on the simulated primary projection data and the raw projection data. Operation 1008 may be performed by the scatter components determination module 440. The scatter components may be determined by subtracting the simulated primary projection data from the raw projection data, then low-frequency filtering or smoothing may be applied to the subtraction result to determine the scatter components. In some embodiments, the scatter components may be determined by subtracting the raw projection data from the simulated primary projection data, then low-frequency filtering or smoothing may be applied to the subtraction result to determine the scatter components.

In 1010, whether the iteration meets the predetermined condition may be determined. Operation 1010 may be performed by the scatter components determination module 440. The predetermined condition may include that desired accuracy is achieved. The predetermined condition may include that convergence is achieved. The predetermined condition may also include that iteration number exceeds default threshold value, e.g., the default threshold value may be the number of 1000. In response to a determination that the iteration meets the predetermined condition, process 1000 may proceed to 1016. In response to a determination that the iteration does not meet the predetermined condition, process 1000 may proceed to 1012.

In 1012, iterated projection data may be obtained based on the scatter components and the raw projection data. Operation 1012 may be performed by the scatter components determination module 440. In some embodiments, the iterated projection data may be obtained by subtracting the scatter components from the raw projection data.

For the second iteration, the iteration number n=1+1=2.

In 1014, the iterated projection data may be designated as the raw projection data. Operations 1004-1010 may be repeated as described above. Similarly, the updated images may then be reconstructed based on the iterated projection data. Simulated primary projection data may be determined based on the updated images via forward projection as described in FIG. 5. Scatter components may be determined by subtracting the simulated primary projection data from the iterated projection data, then low-frequency filtering or smoothing may be applied to the subtraction result to determine the scatter components. The operations aforementioned may be iterated until the desired accuracy is achieved, or convergence is achieved, or the iteration number exceeds a threshold value. After the iteration is stopped, a final scatter components may be determined by the scatter components determination module 440, and may be stored in the storage device 150.

In 1016, corrected projection data may be determined based on a final scatter components and the raw projection data. Operation 1016 may be performed by the corrected projection data determination module 450. In some embodiments, the corrected projection data determination module 450 may retrieve the final scatter components from step 1008 and the raw projection data from step 1002, wherein the final scatter components and the raw projection data could be retrieved from the storage device 150 via, e.g., the network 120. The corrected projection data determination module 450 may determine the corrected projection data by subtracting the final scatter components of the step 1008 from the raw projection data of the step 1002. Thus, the corrected projection data may be substantially scatter-free. In some embodiments, the corrected projection data may be stored in the storage device 150.

The corrected projection data may be used before, during or after the delivery of energy beam. In some embodiments, a corrected image may be reconstructed based on the corrected projection data. In some embodiments, the corrected projection data may be retrieved from the storage device 150. Different reconstruction algorithms may be employed to reconstruct the corrected image based on the corrected second projection data of the subject. Exemplary reconstruction algorithms may include a direct matrix inversion algorithm, an iterative algorithm, a Fourier reconstruction algorithm, a back-projection algorithm, a filtered backprojection algorithm, etc. In some embodiments, the corrected image or the corrected projection data may be used for an electronic portal image device (EPID) based dose verification. In some embodiments, the corrected image or the corrected projection data may be used to provide position information during the IGRT.

It should be noted that the above descriptions of the process 1000 are provided for the purposes of illustration, and are not intended to limit the scope of the present disclosure. For persons having ordinary skills in the art, various modifications and changes in the forms and details of the application of the above method and system may occur without departing from the principles of the present disclosure. In some embodiments, the process 1000 may include one or more other operations. However, those variations and modifications also fall within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system configured to process projection data, comprising:
    at least one non-transitory storage medium including a set of instructions; and
    at least one processor in communication with the at least one non-transitory storage medium, wherein when executing the set of instructions, the at least one processor is configured to direct the system to:
    obtain first projection data corresponding to a first area of a subject;
    obtain second projection data corresponding to a second area of the subject, the first area at least partially overlapping with the second area in an overlapping area;
    determine registered first projection data by registering the first projection data to the second projection data with respect to the overlapping area, wherein the registration of the first projection data to the second projection data is a two-dimensional registration;
    determine a scatter component based on the registered first projection data and the second projection data, the scatter component representing a scatter distribution related to the second projection data; and
    determine corrected second projection data based on the scatter component and the second projection data.

2. The system of claim 1, wherein to obtain first projection data corresponding to a first area of a subject, the at least one processor is further configured to direct the system to:
    obtain a first image generated by performing a first scan to the subject by a first imaging device;
    determine first projection data based on the first image; and
    determine the first projection data based on a physical density distribution related to the first image and a material distribution related to the first image.

3. The system of claim 2, wherein the physical density distribution related to the first image is determined based on at least one pixel value of the first image, wherein the pixel value reflects an extent of absorption of energy beams by an anatomical structure of the subject reflected in the first image, the energy beams being emitted by the first imaging device.

4. The system of claim 2, wherein the at least one processor is further configured to direct the system to:
    segment the first image into one or more regions based on the physical density distribution related to the first image or CT numbers of the first image, each of the one or more regions corresponding to a composition category of the subject; and
    determine the material distribution related to the first image based on the one or more regions corresponding to a composition category of the subject.

5. The system of claim 2, wherein the second projection data is obtained by performing a second scan of the subject using a second imaging device, the second scan is performed using energy beams of one or more energy spectra generated by the second device, and the first projection data is further determined based on the energy spectra and detector energy response of the second device, and to determine first projection data based on the first image and the energy spectra and detector energy response of the second device, the at least one processor is further directed to:
    divide, based on an energy range metric, the energy spectrum of the energy beams related to the second scan into one or more bins, each bin corresponding to an energy range;
    for each of the one or more bins, determine simulated projection data based on the first image and an energy range corresponding to the bin; and
    combine the simulated projection data of the one or more bins to generate the first projection data.

6. The system of claim 5, wherein the simulated projection data of each of the one or more bins correspond to a plurality of voxels, and to determine the simulated projection data corresponding to a bin, the at least one processor is further configured to direct the system to:
    convert the first image into the physical density distribution;
    segment, based on the physical density distribution or CT numbers of the first image, the first image into one or more categories; and
    for each of the one or more bins,
        determine, based on the one or more categories and the energy range corresponding to the bin, a mass attenuation coefficient matrix for the plurality of voxels corresponding to the bin;
        determine, based on the mass attenuation coefficient matrix and the physical density distribution, a linear attenuation coefficient matrix corresponding to the bin; and
        determine, based on the linear attenuation coefficient matrix, the simulated projection data of the bin.

7. The system of claim 5, wherein for each of the one or more bins, the at least one processor is further directed to:
    determine the simulated projection data based on detector energy response corresponding to the energy range.

8. The system of claim 5, wherein the first image includes first isocenter information, and the second scan is performed based on the first isocenter information.

9. The system of claim 1, wherein to determine corrected second projection data based on the scatter component and the second projection data, the at least one processor is further configured to direct the system to:
    divide the scatter component into one or more groups;
    for each of the one or more groups, determine whether a group satisfies a first condition; and
    generate, based on the scatter component of the one or more groups and a result of the determination, a trusted scatter component; and
    determine the corrected second projection data based on the trusted scatter component.

10. The system of claim 9, wherein the first condition is that the scatter component of the each group is positive and lower than a threshold.

11. The system of claim 9, wherein the first condition is that a gradient of the scatter component of the each group is lower than a threshold.

12. The system of claim 9, wherein the first condition is that a ratio of a sum of the registered first projection data in a group and the scatter component in the group to the second projection data in the group is within a certain range.

13. The system of claim 9, wherein:
to generate, based on the scatter component of the one or more groups and a result of the determination, the trusted scatter component, the at least one processor is further configured to direct the system to:
determine the trusted scatter component based on one or more blank portions that are generated by removing, from the scatter component, untrusted projection data of the one or more groups that does not satisfy the first condition; and
to determine the corrected second projection data based on the trusted scatter component, the at least one processor is further configured to direct the system to:
complement the one or more blank portions based on a scatter kernel technique; and
determine the corrected second projection data based on the complemented trusted scatter component.

14. A system configured to process projection data, comprising:
at least one non-transitory storage medium including a set of instructions; and
at least one processor in communication with the at least one non-transitory storage medium, wherein when executing the set of instructions, the at least one processor is configured to direct the system to:
obtain a first image corresponding to a first area of the subject;
obtain second projection data related to an energy spectrum and a detector energy response of a cone-beam computed tomography, the second projection data corresponding to a second area of the subject, the first area at least partially overlapping with the second area in an overlapping area;
determine first projection data based on the first image, the energy spectrum and the detector energy response of the cone-beam computed tomography by dividing the energy spectrum into one or more bins; and
determine a scatter component based on the first projection data and the second projection data.

15. The system of claim 14, wherein to determine the first projection data, the at least one processor is further directed to:
divide, based on an energy range metric, the energy spectrum into one or more bins, each bin corresponding to an energy range;
for each of the one or more bins, determine the simulated projection data based on the first image and an energy range corresponding to the bin; and
combine the simulated projection data of the one or more bins to generate the first projection data.

16. The system of claim 15, wherein the simulated projection data of each of the one or more bins correspond to a plurality of voxels, and to determine the simulated projection data corresponding to a bin, the at least one processor is further configured to direct the system to:
convert the first image into a physical density distribution;
segment, based on the physical density distribution or CT numbers of the first image, the first image into one or more categories; and
for each of the one or more bins,
determine, based on the one or more categories and the energy range corresponding to the bin, a mass attenuation coefficient matrix for the plurality of voxels corresponding to the bin;
determine, based on the mass attenuation coefficient matrix and the physical density distribution, a linear attenuation coefficient matrix corresponding to the bin; and
determine, based on the linear attenuation coefficient matrix, the simulated projection data of the bin.

17. The system of claim 14, wherein the at least one processor is further configured to direct the system to correct the second projection data based on the scatter component, and wherein to correct the second projection data based on the scatter component, the at least one processor is further configured to direct the system to:
divide the scatter component into one or more groups;
for each of the one or more groups, determine whether a group satisfies a first condition; and
generate, based on the scatter component of the one or more groups and a result of the determination, a trusted scatter component; and
correct the second projection data based on the trusted scatter component.

18. The system of claim 17, wherein the first condition is that the scatter component of the each group is positive and lower than a threshold;
the first condition is that a gradient of the scatter component of the each group is lower than a threshold; or
the first condition is that a ratio of a sum of the registered first projection data in a group and the scatter component in the group to the second projection data in the group is within a certain range.

19. A system configured to reduce error in projection data, comprising:
at least one non-transitory storage medium including a set of instructions; and
at least one processor in communication with the at least one non-transitory storage medium, wherein when executing the set of instructions, the at least one processor is configured to direct the system to:
obtain initial projection data by a cone-beam computed tomography;
reconstruct one or more uncorrected images based on the initial projection data;
determine stimulated projection data based on the one or more uncorrected images;
determine scatter components based on stimulated projection data and the initial projection data by subtracting the simulated projection data from the initial projection data;
correct the initial projection data by subtracting the scatter components from the initial projection data to generate corrected initial projection data; and
perform one or more iterations, each current iteration of the one or more iterations including:
assigning the corrected initial projection data of the last iteration as the initial projection data of the current iteration; and
correcting the initial projection data in each current iteration to generate corrected initial projection data according to the process for correcting initial projection data.

* * * * *